United States Patent [19]

O'Brien et al.

[11] Patent Number: 4,637,984
[45] Date of Patent: Jan. 20, 1987

[54] MONOCLONAL ANTI-ORNITHINE DECARBOXYLASE ANTIBODY AND METHOD OF PRODUCING SAME

[75] Inventors: Thomas G. O'Brien, Drexel Hill; Anthony E. Pegg, Hummelstown; Meehard Herlyn, Wynnewood, all of Pa.

[73] Assignees: Wistar Institute of Anatomy and Biology, Philadelphia, Pa.; Research Corporation, Tuscon, Ariz. ; a part interest

[21] Appl. No.: 540,675

[22] Filed: Oct. 11, 1983

[51] Int. Cl.[4] .................. C12N 5/00; C07K 15/04
[52] U.S. Cl. .................................. 435/240; 435/68; 435/70; 435/172.2; 435/241; 435/948; 530/387; 935/104
[58] Field of Search .................. 260/112 R, 112.5 R; 435/68, 70, 172.2, 240, 241, 948; 935/89, 95, 102, 103, 104; 530/387, 388

[56] References Cited

PUBLICATIONS

Pegg, A. E. et al., Biochemical J., vol. 217 (1), pp. 123–128 (1984). Chemical Abstract No. CA100(9):63958X.
Pereson, J. et al., Biochemistry, vol. 23(16), pp. 3777–3783 (1984), Biological Abstract No. 78091134.
Kritsi, Z. et al., Prep. Biochem., vol. 12(5), pp. 445–460, (1982), Chemical Abstract No. CA98(17):139546z.
Persson, L., Acta Chem. Scand., Ser. B, B36(10), pp. 685–688 (1982), Chemical Abstract No. CA98(9):67813j.
Obenrader, M. F. et al., J. Biol. Chem., vol. 252(9), pp. 2866–2872 (1977), Chemical Abstract CA87(3):18184u.
Theoharides, T. C. et al., Folia Biochim. Biol. Graeca, vol. 13, (1–2), pp. 11–23 (1976) in Bio. Abst. 63014972.
Isomaa, V. V. et al., J. Biol. Chem., vol. 258(11), pp. 6735–6740 (1983) in Bio. Abst. 76071825.
Seely, J. E. et al., J. Biol. Chem., vol. 258(4), pp. 2496–2500 (1983) in Bio. Abst. 76046157.
Matsufuji, S. et al., J. Biochem, Tokyo, vol. 96(5), pp. 1525–1530 (1984) in Chem. Abst. 102(1):4280p. (Not Prior Art).

Primary Examiner—Charles F. Warren
Assistant Examiner—M. Moskowitz
Attorney, Agent, or Firm—Howson and Howson

[57] ABSTRACT

Monoclonal anti-ornithine decarboxylase antibody is produced by cell hybrids between hypoxanithine phosphoriboxyltransferase deficient myeloma cells and spleen cells derived from an animal previously immunized with ornithine decarboxylase. By means of immunoaffinity chromatography using cyanogen bromide-activated agarose coupled with the antibody, ornithine decarboxylase in animal cell extracts can be highly purified in high yield.

8 Claims, 5 Drawing Figures

MONOCLONAL ANTI-ORNITHINE DECARBOXYLASE ANTIBODY AND METHOD OF PRODUCING SAME

The work resulting in the invention herein described and claimed was supported by grants from the National Institutes of Health.

SUMMARY OF THE INVENTION

This invention relates to monoclonal anti-ornithine decarboxylase antibody, to novel hybridoma cells which express such antibody, and to a method for producing such hybrid cells and anti-ornithine decarboxylase antibody.

BACKGROUND OF THE INVENTION

Ornithine decarboxylase (ODC) is the initial step in the mammalian polyamine biosynthetic pathway (Pegg and Williams-Ashman, Polyamines in Biology and Medicine, pp. 3-42, Marcel Dekker, New York (1981); Pegg and McCann, Am. J. Physiol. 243: C212-C221 (1982). This enzyme exhibits rapid and many fold changes in activity in response to a wide variety of stimuli and there is evidence that stimulation may be linked to cell growth and tumor promotion (Boutwell et al., Adv. Enzyme Reg. 17: 89-112 (1979)); Russell, Pharmacology 20: 117-129 (1980); Pegg and McCann, (1982 supra.). Detailed studies of the underlying biochemical mechanism of the regulation of ornithine decarboxylase have been hampered by the small amounts of this protein present in mammalian tissues (Pritchard et al., Biochem. Biophys. Res. Commun. 100: 1597-1603 (1981)); Seely et al., Biochem. J. 206: 311-318 (1982) and the consequent difficulty in obtaining the purified protein. Recently, several groups have described the purification of ornithine decarboxylase to homogeneity from rat liver (Kameji et al., Biochem. Biophys. Acta 717: 111-117 (1982)); Kitani, et al, J. Bio. Chem. 258: 235-239 (1983)) or mouse kidney (Persson, Acta Chem Scand. 35: 737-738 (1981); Seely et al., Biochemistry 21: 3394-3399 (1982) and specific antisera have been raised to purified enzyme in rabbits (Persson, Acta Chem. Scand 36: 685-688 (1982)); Seely, et al J. Bio Chem. 258 2496-2500 (1983). However, even from these relatively rich sources of the enzyme, only small amounts of it were obtained and improved methods of isolating the enzyme from crude extracts were needed to study the enzyme in other cell extracts.

Fusion between myeloma cells and spleen cells from immunized donors has been shown to be a successful method of deriving homogenous antibodies. Thus, continuous cell lines of genetically stable hybridoma cells capable of producing large amounts of monoclonal antibodies against maligant tumors and specific viruses and their antigenic determinants have been developed. More particularly, according to U.S. Pat. No. 4,172,124 to Koprowski et al, antibodies demonstrating a specificity for malignant tumors can be produced by somatic cell hybrids between hypoxanthine phosphoriboxyl-transferase deficient myeloma cells and spleen or lymph cells derived from an animal previously primed with tumor cells. Also, according to U.S. Pat. No. 4,196,265 to Koprowski et al., continuous cell lines of genetically stable fused cell hybrids capable of producing large amounts of monoclonal antibodies against specific viruses and their antigenic determinants have been developed.

It would be desirable if such cell fusion techniques could be employed to provide a reliable and standard supply of anti-enzyme antibodies, e.g. anti-ODC antibodies, which in turn could be used to react with mammalian ODC, as for example in an immunoaffinity column, from which the active enzyme could then be eluted, recovered and used for the study of polyamine synthesis and its regulation during cell growth.

BRIEF DESCRIPTION OF THE INVENTION

This invention contemplates a novel continuous hybridoma cell line which expresses monoclonal anti-ODC antibody, to the use of such cell line in production of such antibody, and to a method for producing such cell line. The invention also contemplates a method for obtaining large amounts of ODC for use in the study of polyamine synthesis and cell growth.

DETAILED DESCRIPTION OF THE INVENTION

According to the present invention a novel continuous hybridoma cell line which expresses anti-ODC antibody is obtained by immunizing an animal with ODC, preferably purified ODC, forming fused hybrid cells between antibody-producing cells from the immunized animal and myeloma cells, cloning the hybrids and selecting clones which express anti-ODC antibody. More specifically, a mouse or other animal is injected with purified ODC and the antibody producing cells of the animal's spleen are then fused with a cancerous type of mouse cell or myeloma cell. The hybrid cell so formed produces the anti-ODC antibody molecule of its spleen cell parent and continually grows and divides like its parent myeloma cell. The clone of cells producing such antibody are selected and grown as a continuous cell line from which large amounts of anti-ODC antibody is harvested.

In the alternative the clonal hybrid cells may be injected into a histocompatable animal where they proliferate, producing high levels of anti-ODC antibody which can be recovered from the animal's ascites fluid.

Thus, the present invention makes available on a relatively large scale a reliable and standard supply of anti-ODC antibody for use in the immunolocalization of antigen in normal, premalignant and malignant tissues; purification of ODC from difficult sources via immunoaffinity chromatography; as an aid in the synthesis of cDNA from ODC mRNA and cloning of the gene for ODC, and immunodiagnosis of tumors.

These and other advantages of this invention will become further apparent from the following detailed description, specific examples, and drawings in which.

Figure 1:
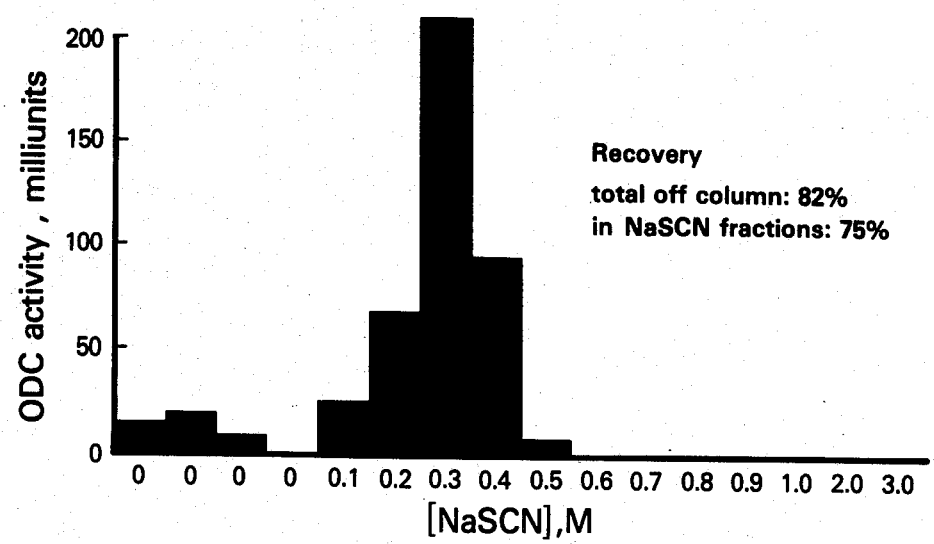
FIG. 1 is a graph in which recovery of mouse kidney ODC by immunoaffinity chromatography using anti-ODC antibody-bound affinity sorbent is shown by plotting ODC activity vs. concentration of sodium thiocyanate eluant.
Figure 2:
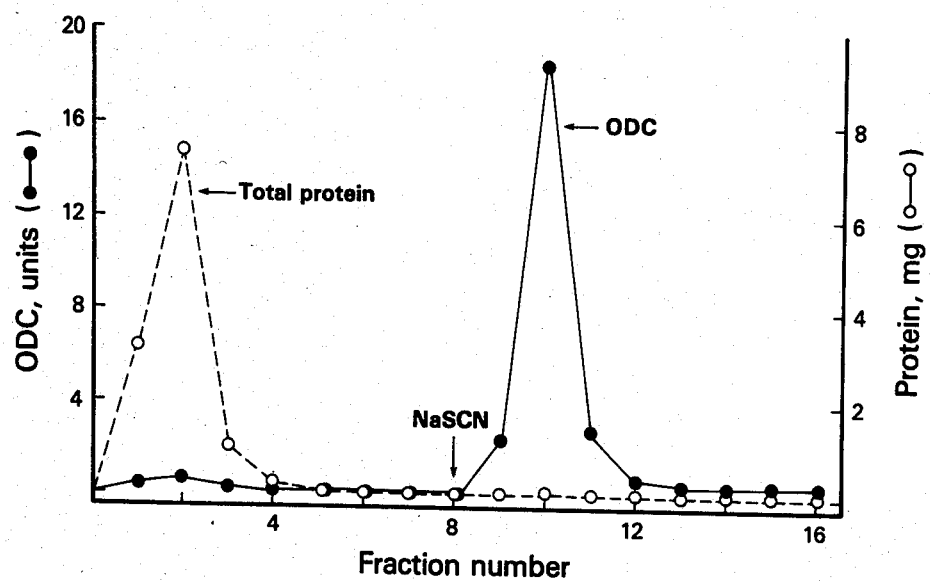
FIG. 2 is a graph in which total protein and ODC recovery from mouse kidney extracts using an immunoaffinity chromatography column containing anti-ODC antibody-bound affinity sorbent is shown by plotting fraction number vs. ODC activity and protein (mg.), the eluant in fractions 8-12 being sodium thiocyanate.
Figure 3:
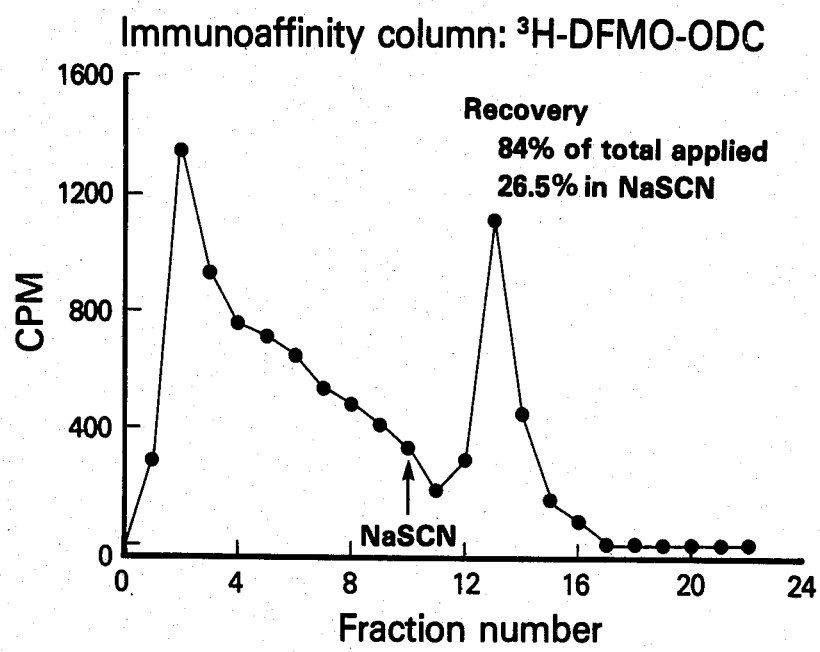
FIG. 3 is similar to FIG. 2 and was obtained using the same general procedure as that used in plotting FIG. 2, except that [5-$^3$H]α-difluoromethylornithine (DFMO)- labeled ODC was chromatographed and elution was carried out using 0.4M NaSCN (see arrow)
Figure 4:
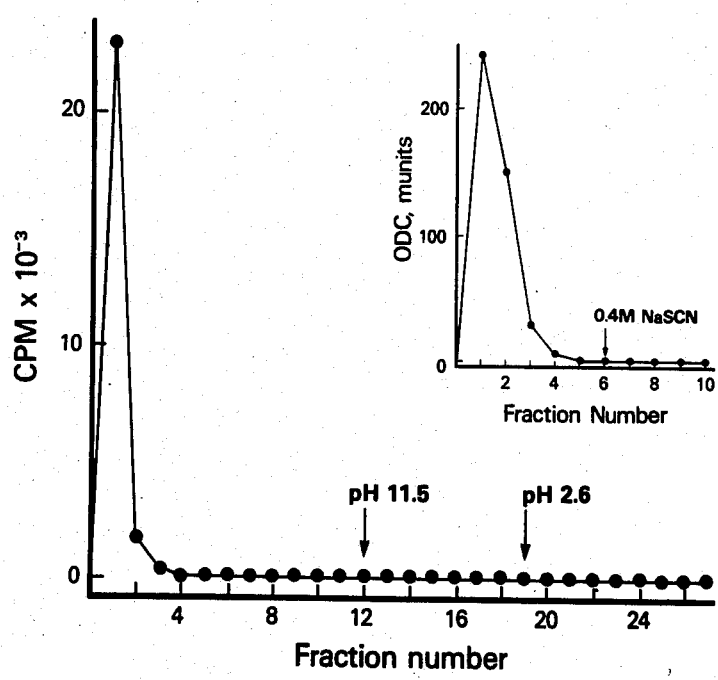
Figure 5:
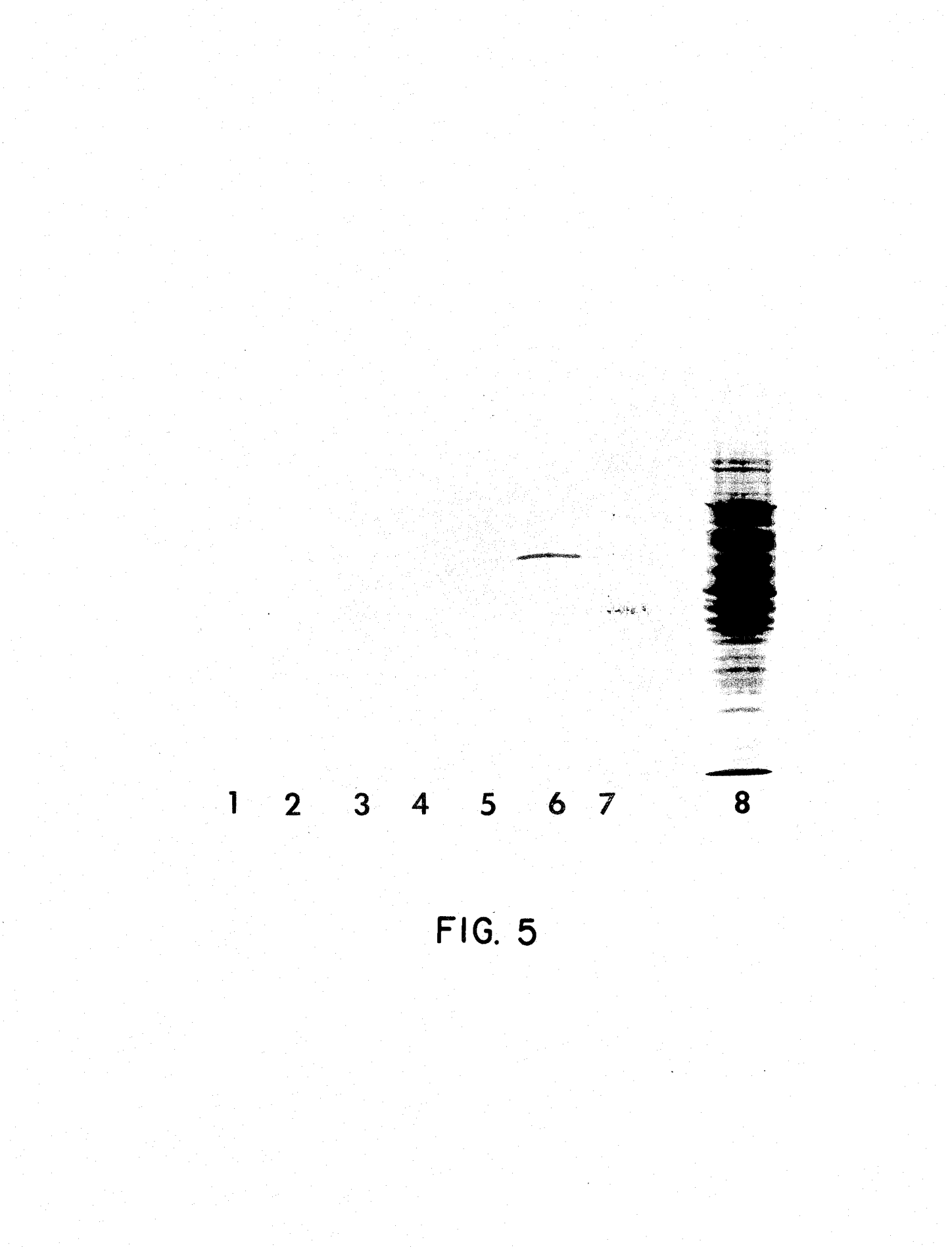

FIG. 4 is a plot of CPM×$10^{-3}$ vs. fraction number for [5-$^3$H]DFMO-labeled ODC using immunoaffinity chromatography columns prepared in the same way as those used in obtaining the data plotted in FIGS. 1-3, except the antibody bound to the sorbent was 1116NS10, an IgG directed against the Le$^b$ human blood group antigen. The inset graph obtained by using the immunoaffinity chromatography procedure used to obtain the data plotted in FIG. 2, except fewer fractions were collected, and FIG. 5 shows the results obtained by means of polyacrylamide gel electroporesis of labeled ODC precipitated by the monoclonal anti-ODC antibody produced according to the method of this invention.

The following is a typical procedure for preparing a hybrid cell line which produces anti-ODC antibodies, and the procedural steps are generally known. While this procedure refers to fusing myeloma cells of a BALB/c mouse with the spleen cells of BALB/c mice primed with ODC, the procedure is applicable using myeloma cells and anti-ODC antibody producing cells from another source.

A. PREPARATION OF SPLEEN CELLS FOR FUSION

The enzyme ornithine decarboxylase was purified from kidneys of androgen-treated mice through pyridoxamine-Sepharose affinity chromotography using the technique as described by Seely et al in *Biochemistry* 21: 3394-3399 (1982). The enzyme was about 10-20% pure, based on the comparison of its specific activity with that of the homogeneous enzyme Seely et al, *Biochemistry*, supra. The enzyme was used to immunize a BALB/c female mouse by subcutaneous admistration of about 5 μg emulsified in Freund's complete adjuvant. The mouse was reimmunized 4 weeks later with a further 5 μg of the enzyme in incomplete adjuvant given intraperitoneally. After an additional 4 weeks, 5 μg of the enzyme were administered intravenously, and 4 days later the mouse was sacrified and a spleen cell suspension was prepared in the manner taught by Gerhard et al., *Eur. J. Immunol.* 5: 720-725 (1975). Red blood cells were lysed by incubation of 15 minutes at 4° C. in NH$_4$Cl (0.83%). The resulting cell suspension was washed by one centrifugation (800×g) through heat-inactivated calf serum and one centrifugation in protein-free medium (RRMI 1640, buffered with 7.5 mM HEPES, pH 7.2).

B. PREPARATION OF MYELOMA CELLS FOR FUSION

BALB/c (P3×63 Ag8-variant 653) myeloma cells derived from the MOPC-21 line and deficient in HPRT (E.C.2.4.2.8) as described by Kearney et al *J. Immunol* 123: 1548-1550 (1979), were maintained in Eagle's minimum essential medium (MEM) containing 10% fetal calf and 10% horse serum. The growth of P3×63 Ag8 myeloma cells is inhibited by selective hypoxanthine-aminopterin-thymidine (HAT) medium.

C. PRODUCTION OF HYBRIDS

Production of hybrids was accomplished by mixing $10^7$ BALB/c (P3×63 Ag8) myeloma cells with $10^8$ spleen cells obtained from the ODC immunized BALB/c mouse. The cell mixture was centrifuged at 800×g and the cells were resuspended for fusion in a 50% solution (w/v) of polyethylene glycol (PEG 4000) diluted in minimum essential medium (MEM) without serum following the procedure described by Koprowski et al., *Proc. Natl. Acad. Sci. USA* 74: 2985-2988 (1977), and by Herlyn et al., *Proc. Natl. Acad. Sci. USA* 76: 1438-1442 (1979). The resulting hybridoma cells designated B 11 were cloned in hypoxanthine-aminopterin-thymidine (HAT) medium by limiting dilution as described by Galfré and Milstein *Meth. Enzymol.* 73: 3-46 (1975).

D. KARYOLOGICAL ANALYSIS

The P3×63 Ag8 parental cells contained an average of 63 chromsomes and BALB/c spleen cells an average of 40 chromosomes.

The Hybridoma cell line designated B 11 was deposited with The Wistar Institute of Anatomy and Biology, Philadelphia, Pa., U.S.A. on Oct. 12, 1982 and with the American Type Culture Collection (ATCC), Rockville, Md., U.S.A., Deposit Accession No. ATCC HB 8372, on Oct. 5, 1983. The deposits are available pursuant to the patent laws and regulations of the United States and of those countries foreign to the United States in which counterparts of this application are filed. The availability of a deposit does not constitute a license to practice the invention of this application in derogation of any patent issued thereon or on any division or continuation of this application.

E. TESTING OF THE CLONES FOR PRODUCTION OF ANTI-ODC ANTIBODY

Polyvinyl chloride microtiter 96 well plates (Dynatech, Alexandria, VA) were coated with 50-100 μg second antibody (goat anti-mouse IgG) by addition of a solution of 0.05M borate buffer, pH 8 which was allowed to dry overnight at room temperature. After washing the wells three times with RIA buffer (phosphate buffered saline (PBS), 0.12M NaCl, 0.012M Na$_2$PO$_4$, 0.0015M KH$_2$PO$_4$, containing 10% agamma globulin horse serum and 0.08% sodium azide), 0.05 ml of the culture supernatants were added and incubated at 4° C. overnight. The supernatant was removed after washing three times with RIA buffer and 0.05 ml of a solution containing about 10,000 cpm [5-$^3$H]α-difluoromethyl ornithine (DFMO)-labled ornithine decarboxylase. This labeled protein was prepared by reacting the partially purified mouse kidney enzyme ODC with [5-$^3$H]DFMO (15 Ci/mmol) as described by Seely et al., *J. Biol. Chem.* 258: 2496-2500 (1983). Incubation was continued for at least 1 hour at room temperature or overnight at 4° C. The solution was then removed, the wells washed 3 times with RIA buffer and their contents solubilized in 0.5N NaOH and counted. Controls for non-specific binding were included by omitting either the second antibody or the culture supernatant. Less than 20-30 cpm was bound under these conditions. One clone B 11 which gave a strong positive response binding about 500 cpm of the labeled antigen was re-cloned several times and grown up as described above. The immunoglobulin produced by this clone and designated MK-1 was found to be of the IgM type by Ouchterlony immunodiffusion analysis using monospecific antisera purchased from Bionetics, Bethesda, MD. The commercial goat anti-mouse IgG preparation used in the initial screening has significant ability to bind mouse IgMs also, and this accounts for the initial detection of the MK-1 antibody.

The hybridoma cells B 11 were grown as an ascites form by intraperitoneal injection into pristane-treated mice (Galfré and Milstein, *Meth. Enzymol.* 73 (part B) 1-46 (1981)), and the resulting ascites fluid was used as a source of the monoclonal antibody MK-1.

F. PRECIPITATION OF ORNITHINE DECARBOXYLASE AND [5-$^3$H]DFMO-ORNITHINE DECARBOXYLASE

Mouse kidney ornithine decarboxylase (about 30 units in 0.1 ml of buffer A which consists of 25 mM Tris-HCl, pH 7.5, 0.1 mM EDTA and 2.5 mM dithiothreitol) was incubated with 0.06 ml of various dilutions of ascites fluid containing monoclonal antibody MK-1 (diluted into 150 mM Tris-HCl, pH 7.5, 1 mM EDTA, 0.02% Brij 35; buffer A) for 2 hours at 0°-4° C. A further 0.06 ml of a solution (3 mg/ml) of goat anti-mouse IgM was then added and the samples shaken gently overnight at 0°-6° C. 0.08 ml of a 10% suspension of protein A bacterial adsorbent (Miles Laboratories, Elkhart, IN) was then added and the samples shaken for 2 hours at 0°-6° C. After centrifugation at 15,000×g for 1 minute, 0.1 ml aliquots of the supernatant were assayed for ornithine decarboxylase activity. The precipitation of [5-$^3$H]DFMO-ornithine decarboxylase was carried out in the same way starting with a solution containing 2952 cpm in 0.1 ml. The immunoprecipitate was washed twice in 0.5 ml of buffer A, resuspended in 0.2 ml water and counted as previously described (Seely et al, 1983 supra). Control experiments using another ascites fluid containing monoclonal IgM (designated 1116NS10) which was prepared against a human adenocarcinoma cell line (Brockhaus et al., *J. Biol. Chem.* 256: 13,223-12,225 (1981)) indicated no loss of orithine decarboxylase activity or precipitation of the [5-$^3$H]DMFO-ornithine decarboxylase under these conditions. A positive control was provided by the use of rabbit antiserum against orithine decarboxylase. This was used in the same way, but the goat anti-mouse IgM was omitted.

A major advantage of the hybridoma technique for production of anti-ODC antibody is that a homogeneous antigen is not required for immunization, and in the experiments herein described only partially purified ornithine decarboxylase protein was used. However, it is necessary to have either the purified protein of interest or a specific way to identify its binding to the antibodies in order to screen potential clones of antibody-secreting cells. Such identification was achieved by using [5-$^3$H]DFMO to specifically label ornithine decarboxylase. DFMO is an enzyme-activated irreversible inhibitor of ODC and forms a covalent bond with the enzyme. This interaction is extremely specific and even in crude cell extracts ornithine decarboxylase is the only protein which becomes labeled (Seely et al., (1982) supra). The use of [5-$^3$H]DMFO-labeled ornithine decarboxylase to identify positive clones helped in the isolation of anti-ODC antibody designated MK-1, which recognized the native enzyme since the solution antigen was used for detection rather than insolubilized protein used in many ELISA techniques. However, it is unlikely that antibodies directed at the active site of ornithine decarboxylase would be found using this screening method since DFMO binds at the active site. When added to solutions containing either native ornithine decarboxylase from rat or mouse tissues or [5-$^3$H-DFMO]-labeled ornithine decarboxylase, the monoclonal antibody, MK-1, did not lead to rapid loss of the activity or precipitation of the radioactivity. However, precipitation was achieved by addition of a second antibody (IgG) specific for mouse IgM followed by protein A (see Table 1, below).

TABLE 1

Precipitation of Ornithine Decarboxylase by Monoclonal Antibody MK-1

Example A. Precipitation of Native Enzyme

| Antibody added (0.06 ml of dilution shown) | Ornithine Decarboxylase Activity Remaining (units) | Percent Precipitated |
|---|---|---|
| None | 27.1 | 0 |
| Rabbit antiserum (1:50) | 0.1 | 99 |
| Monoclonal antibody (1:50) | 8.7 | 68 |
| Monoclonal antibody (1:100) | 8.9 | 67 |
| Monoclonal antibody (1:500) | 8.8 | 68 |
| Monoclonal antibody (1:2500) | 22.7 | 16 |

Example B. Precipitation of Enzyme which has been Labeled and Inactivated by Reaction with [5-$^3$H]DFMO

| Antibody added (0.06 ml of dilution | [5-$^3$H]DFMO-Labeled Ornithine Decarboxylase Precipitated (cmp)* | Percent Precipitated |
|---|---|---|
| None | 0 | 0 |
| Rabbit antiserum (1:50) | 2756 | 93 |
| Monoclonal antibody (1:50) | 2133 | 72 |
| Monoclonal antibody (1:500) | 1153 | 39 |
| Monoclonal antibody (1:2500) | 250 | 8 |

*A total of 2952 cpm was added.

Referring to Table 1, it will be noted that not all of the ornithine decarboxylase was precipitated under the latter described conditions and the amount precipitated being somewhat variable from experiment to experiment. In Example A of Table 1 using mouse kidney extracts which contained about 25 ng of ornithine decarboxylase in 0.1 ml, approximately 70% of the activity was precipitated by about 1:500 fold dilutions of the ascites fluid. Increasing the antibody concentration by 10-fold did not increase the extent of precipitation, but all of the enzyme could be precipitated by polyclonal rabbit antiserum under the same conditions. In the experiment, the monoclonal antibody, MK-1, was incubated with enzyme for 2 hours at 4° C., but increasing the time or temperature did not increase the percentage precipitated.

Similiarly, the monoclonal antibody MK-1 was able to precipitate about 70% of the radioactivity present in [5-$^3$H]DFMO-labeled ornithine decarboxylase in the presence of the second antibody and protein A, although rabbit antiserum could precipitate more than 90% of this material (Example B, Table 1). Larger amounts of the monoclonal antibody were needed to bring about precipitation of the inactivated labeled antigen than of the native enzyme (see Table 1).

G. IMMUNOAFFINITY CHROMATOGRAPHY TESTS

The MK-1 antibody was purified from ascites fluid by ammonium sulfate precipitation and gel filtration on Sephacryl S-300 (Hudson, et al., *Practical Immunology*, Blackwell Scientific Publications, Oxford pp. 221-222 (1980)). Fractions eluted from this column containing pure antibody (determined by polyacrylamide gel electrophoresis under denaturing conditions) were used to prepare immunoaffinity columns. Cyanogen bromide-activated Sepharose 4B was reconstituted and washed according to the manufacturer's instructions. It was then coupled with the MK-1 antibody by overnight incubation and the antibody (2–5 mg protein/ml) in PBS, pH 8.0. Determination of the $A_{280}$ of the solution before and after coupling indicated that about 80–95% of the antibody was coupled to the Sepharose. Remaining sites on the gel were blocked by reaction with 0.5M ethanolamine at room temperature for several hours or overnight at 4° C. Columns containing about 2 ml of the gel were prepared, washed and buffer A containing 0.3 mM L-ornithine and 20M pyridoxal phosphate and stored at 4° C. until use.

Experiments using immunoaffinity columns containing bound MK-1 antibody prepared as described above showed that both active ornithine decarboxylase and the [5-$^3$H]DFMO-labeled derivative were retained on these columns. Several different strategies for eluting the material from these columns were tested. Low ionic strength buffer of either high (11.5) or low (2.5) pH eluted the protein, but were not compatible with recovery of enzyme activity in good yield. However, as shown in FIG. 1, a stepwise gradient of the chaotropic agent NaSCN eluted the enzyme with excellent retention of activity (measured after dialysis to remove the thiocyanate). About 82% of the enzyme activity applied was recovered with 91.5% of this amount (75% of the total) in the NaSCN fractions.

In obtaining the data plotted in FIG. 1, partially purified mouse kidney ornithine decarboxylase (through DEAE cellulose chromatography) was applied to an immunoadsorbant column prepared as described above. The column was eluted with 2 ml fractions of buffer A containing 0.3 mM L-ornithine and 20 μM pyridoxal phospate (loading buffer) containing the concentration of NaSCN shown in FIG. 1, and the ornithine decarboxylase (ODC) activity eluted determined after overnight dialysis against 60 volumes of buffer A to remove NaSCN.

The immunoaffinity chromatography columns can also be used to purify crude preparations of ornithine decarboxylase (see FIG. 2). After application of a crude mouse kidney extract, virtually all of the protein was eluted in the first 4 fractions (curve with open circles), while 93% of the recovered ornithine decarboxylase activity was eluted as a sharp peak when 1M NaSCN in loading buffer (see arrow) was applied (curve with solid dots). Even with the crude extracts which had been fractionated only by ammonium sulfate precipitation (Seely et al., *Biochemistry* 21: 3394–3399 (1982)) at least 60-fold purification was achieved by a single pass through the immunoaffinity column (FIG. 2). When the extracts were partially purified by DEAE-cellulose chromatography (Seely, et al., (1982 supra)) prior to immunoaffinity chromatography at least 2000-fold purification was achieved.

Referring to FIG. 3, the same procedure as used in obtaining the data for FIG. 2 was employed except [5-$^3$H]DFMO-ornithine decarboxylase was chromatographed and elution was carried out with 0.4M NaSCN (arrow). Approximately 84% of the applied radioactivity was recovered from the column and 26.5% in the peak after 0.4M NaSCN. However, a lesser fraction of the labeled ornithine decarboxylase was retained by the column. This result is consistent with the results of Table 1 and other data suggesting that the monoclonal antibody MK-1 has a higher affinity for unmodified ornithine decarboxylase than for the DFMO-inactivated protein.

The immunoaffinity columns prepared as above could be reused several times without significant loss of acitvity. Immunoaffinity columns prepared in the same way with a mouse monoclonal IgM (1116NS10) directed against the Le$^b$ blood group antigen (Brockhause et al., (1981 supra)) did not retain native or DFMO-labeled ornithine decarboxylase (FIG. 4) indicating that the results are not due to a non-specific adherence of ornithine decarboxylase to the column adsorbent.

In FIG. 4 the large graph shows results with [5-$^3$H]DFMO-labeled ornithine decarboxylase which was applied in loading buffer and eluted first with this buffer and then with 50 mM diethylamine, pH 11.5 and by 50 mM acetate, pH 2.6 (treatments known to release the labeled enzyme from MK-1 antibody columns). The recovery of radioactivity was about 85%. The inset in FIG. 4 shows chromatography of partially purified ornithine decarboxylase in the same manner as FIG. 2, except that fewer fractions were collected. The recovery of ornithine decarboxylase activity was 96% of that applied.

H. IMMUNOPRECIPITATION OF LABELED ORNITHINE DECARBOXYLASE FROM MICE TREATED WITH [$^{35}$S]METHIONINE

Female BALB/c mice were untreated or treated with androgens to induce ornithine carboxylase as previously described (Seely and Pegg, (1983), supra)). The mice were then given 500 μCi of [$^{35}$S]methionine (1284 Ci/mmol) by intraperitoneal injection of a 0.2 ml solution in PBS. The mice were sacrificed 30 minutes later and the kidneys removed, homogenized in 3 vol. of 25 mM Tris-HCl, pH 7.5, 0.1 mM EDTA, 2.5 mM dithiothreitol and centrifuged at 100,000×g for 45 min. Aliquots of 0.05 ml of the supernatant were incubated with 0.15 ml of a 1:50 dilution of the MK-1 ascites fluid (diluted in buffer A) for 3 hours at 0°–4° C. Thirty μl of a solution (30 mg/ml) of goat anti-mouse IgM was then added and incubation continued overnight at 0°–4° C. After 16 hours, bacterial protein A adsorbent (0.3 ml of 10% solution) was added and the sample incubated with shaking for an additional 2 hours at room temperature. The mixture was diluted by additon of 0.75 ml of buffer A and centrifuged at 15,000×g for 30 seconds. The pellet was washed 4 times in buffer A and finally resuspended in 0.1 ml of a solubilizing buffer containing 2% sodium dodecyl sulfate, 5% 2-mercaptoethanol, 10% glycerol and 62.5 mM Tris-HCl, pH 6.8. After heating in a boiling water bath for 5 minutes the sample was centrifuged at 15,000×g for 1 minute and the supernatant used for polyacrylamide gel electrophoresis on a 10% discontinuous buffer system of Laemmli (1970). The gel was fixed overnight in 10% trichloroacetic acid, 10% glacial acetic acid, 30% methanol, impregnated with EN$^3$HANCE dried and exposed to Kodak XAR-5 X-ray film at −70° C. for 3 days. Control samples using either a monoclonal antibody not directed against ornithine decarboxylase or a polyclonal rabbit antiserum to ornithine decarboxylase were prepared in the same way.

The foregoing experiment showed that the monoclonal antibody in conjunction with protein A could be used to demonstrate the rapid synthesis of ornithine decarboxylase in the kidneys of androgen-treated female mice. As shown in FIG. 5, a band of labeled protein having a M.W. of about 55,000 could be precipitated from extracts of kidneys of such mice given [$^{35}$S]methionine, 30 minutes before death (Lanes 2 and 7). As shown in Lane 3, this band was not present in similarly treated extracts from female mice not treated with androgens which have a 400-fold lower content of ornithine decarboxylase (Seely and Pegg, (1983), supra)). The band corresponded exactly to a marker of [5-$^3$H]DFMO-labeled ornithine decarboxylase (Lane 5) and to a band precipitated by polyclonal rabbit antiserum to ornithine decarboxylase (Lane 6). This band was not found when another monoclonal antibody (1116NSID) not directed against ornithine decarboxylase was used as a control (Lanes 1 and 4). The band precipitated by the rabbit antiserum (Lane 6) was more intense than that precipitated by MK-1 (2 and 7) which is consistent with the more complete precipitation of ornithine decarboxylase by the rabbit antiserum. However, the bands had identical mobility. A vancant lane was left between lanes 7 and 8 to allow for some contamination by the very heavily labeled total extract sample placed in Lane 8.

The immunoaffinity purification described in this specification may be used in the isolation of ornithine decarboxylase from mammalian cell extracts in which this enzyme represents only a very small percentage of the total protein. Although the species specificity of the interaction of the monoclonal antibody MK-1 has not been investigated in detail, it does interact with the enzyme ODC from mouse, rat and hamster tissues, and cells from these species could be used as sources of enzyme. Although the degree of precipitation of the enzyme by the monoclonal antibody was somewhat variable, the experiments provided no evidence in favor of multiple forms of the enzyme. The labeled band of ornithine decarboxylase precipitated by the monoclonal antibody from kidney extract of mice given [$^{35}$S]methionine coincided exactly with the band precipitated by the polyclonal rabbit antiserum and with the [5-$^3$H]DFMO labeled marker of ornithine decarboxylase. The substantial incorporation of [$^{35}$S]methionine into this band provides direct experimental evidence showing that ornithine decarboxylase has a rapid rate of synthesis and degradation. Ornithine decarboxylase represents only 1 part in 5-10,000 of the soluble protein in the mouse kidney even after androgen stimulation, but the radioactivity incorporated into the ornithine decarboxylase band amounts to about 1% of the total incorporation into protein. This indicates that the enzyme protein must turn over much more rapidly than the average kidney protein. These results, therefore, confirm previous reports based on indirect evidence that ornithine decarboxylase protein has a very short half life. In vitro studies of the mechanism by whch the rapid degradation of ornithine decarboxylase is brought about should be aided by the availability of the radioactively labeled protein. This substrate can now be prepared by administration of [$^{35}$S]methionine to androgen-treated mice followed by immunoaffinity chromatography of the kidney extracts.

MATERIALS

L-[1-$^{14}$C]Ornithine (57 Ci/mol), DL-[5-$^3$H]α-difluoromethylornithine (15 Ci/mmol) and L-[$^{35}$S]methionine (1284 Ci/mmol) and EN$^3$HANCE were obtained from NEN, Boston, Mass. Bacterial protein A absorbent was obtained from Miles Laboratories, Elkhart, IN. Cyanogen bromide-activated Sepharose was purchased from Pharmacia Fine Chemicals, Piscataway, N.J. Other reagents came from Sigma Chemical Co., St. Louis, MO.

What is claimed is:

1. A continuous cell line which produces a monoclonal antibody of the IgM type which specifically binds to rodent ornithine decarboxylase antigen comprising a fused cell hybrid of rodent spleen cells immunized with rodent ornithine decarboxylase antigen, and rodent myeloma cells.

2. The continuous cell line of claim 1 which upon being cloned in vitro in hypoxanthine-aminopterin-thymidine medium produces said monoclonal antibody of the IgM type.

3. The continuous cell line of claim 1 which produces said monoclonal antibody of the IgM type in vivo by injection of said cells of said cell line into a histocompatable animal from which said antibody is capable of being recovered from the ascites fluid of said animal.

4. The continuous cell line of claim 1 comprising a fused cell hybrid of mouse spleen cells and mouse myeloma cells.

5. The continuous cell line of claim 4 in which said mouse spleen cells are immunized with purified mouse kidney ornithine decarboxylase antigen.

6. A continuous mouse hybrid cell line having the identifying characteristics of ATCC HB 8372.

7. A rodent IgM monoclonal antibody, which binds to rodent ornithine decarboxylase, produced by a continuous cell line comprising a fused hybrid of rodent spleen cells immunized with rodent ornithine decarboxylase antigen, and rodent myeloma cells.

8. A mouse IgM monoclonal antibody, which binds to rodent ornithine decarboxylase, produced by a cell line having the identifying characteristics of ATCC HB 8372.

* * * * *